(12) United States Patent
Chandra et al.

(10) Patent No.: US 7,988,954 B2
(45) Date of Patent: Aug. 2, 2011

(54) HAIR TREATMENT COMPOSITION COMPRISING SUGAR LACTONE

(75) Inventors: Lalitesh Chandra, Wirral (GB); Rebecca Justine Elliott, Bebington (GB); Anand Ramchandra Mahadeshwar, Wirral (GB); Laxmikant Tiwari, Southampton (GB)

(73) Assignee: Conopco, Inc., Englewood Cliffs, NJ (US)

( * ) Notice: Subject to any disclaimer, the term of this patent is extended or adjusted under 35 U.S.C. 154(b) by 741 days.

(21) Appl. No.: 10/592,225

(22) PCT Filed: Feb. 11, 2005

(86) PCT No.: PCT/EP2005/001408
§ 371 (c)(1),
(2), (4) Date: Jun. 25, 2007

(87) PCT Pub. No.: WO2005/084622
PCT Pub. Date: Sep. 15, 2005

(65) Prior Publication Data
US 2007/0298003 A1    Dec. 27, 2007

(30) Foreign Application Priority Data

Mar. 8, 2004  (EP) .................... 04251324
Mar. 11, 2004 (EP) .................... 04251394

(51) Int. Cl.
*A61Q 5/04* (2006.01)
*A61Q 5/02* (2006.01)

(52) U.S. Cl. .................... 424/70.2; 424/70.12

(58) Field of Classification Search ........... None
See application file for complete search history.

(56) References Cited

U.S. PATENT DOCUMENTS

| | | | | |
|---|---|---|---|---|
| 3,470,887 | A | | 10/1969 | Kremer et al. .................... 132/7 |
| 4,363,815 | A | * | 12/1982 | Yu et al. .................... 514/263.31 |
| 4,380,549 | A | * | 4/1983 | Van Scott et al. .............. 514/23 |
| 4,911,919 | A | | 3/1990 | Patel et al. ...................... 424/70 |
| 5,425,938 | A | * | 6/1995 | Znaiden et al. ........... 424/78.02 |
| 5,641,477 | A | | 6/1997 | Syed et al. .................. 424/70.4 |
| 5,641,480 | A | * | 6/1997 | Vermeer .................... 424/70.24 |
| 6,384,079 | B1 | | 5/2002 | Yu et al. ........................ 514/577 |
| 2003/0105169 | A1 | | 6/2003 | Lennon ............................ 516/53 |
| 2003/0147828 | A1 | * | 8/2003 | Bracken et al. ........... 424/70.12 |

FOREIGN PATENT DOCUMENTS

| | | |
|---|---|---|
| DE | 697 634 | 10/1940 |
| DE | 1 201 951 | 9/1965 |
| EP | 455 185 | 11/1991 |
| EP | 530 974 | 7/1995 |
| GB | 915 816 | 1/1963 |
| WO | 00/42978 | 7/2000 |
| WO | 02/43675 | 6/2002 |
| WO | 2004/037305 | 5/2004 |

OTHER PUBLICATIONS

PCT International Search Report in a PCT application PCT/EP2005/001408.
PCT International Search Report in a PCT application PCT/EP2005/001822.
Derwent Abstract—JP 2002 356408 published Dec. 13, 2002.
Derwent Abstract—JP 2001 233746 published Aug. 28, 2001.
Co-pending application: Applicant: Elliott et al., U.S. Appl. No. 10/592,221.

* cited by examiner

*Primary Examiner* — Jyothsna Venkat
(74) *Attorney, Agent, or Firm* — Ronald A. Koatz

(57) ABSTRACT

An aqueous hair treatment composition comprising: a) from 0.01% to 10% by weight of the total composition of beeswax; and b) from 0.01% to 10% by weight of the total composition of a sugar lactone.

3 Claims, No Drawings

HAIR TREATMENT COMPOSITION COMPRISING SUGAR LACTONE

FIELD OF THE INVENTION

The present invention relates to hair treatment compositions. In particular it relates to hair treatment compositions that straighten hair.

BACKGROUND AND PRIOR ART

Style and fashion considerations can lead to changes in the desired condition/appearance of the hair. One group of consumers desires hair which is straighter and easier to manage after treatment: by this is meant reduced hair volume, less fluffiness and greater mutual alignment of the hairs.

Hair straightening compositions have been around for some time. Many of the compositions that are on the market are based on chemical treatment of the hair in a two-step process using thiol- or hydroxide-based reducing agents followed by a neutralisation or oxidation step. Such systems have various negatives associated with them; in that the process itself takes a relatively long time and is difficult to conduct, in many instances this straightening process is undertaken by a qualified hairdresser in a professional salon. Furthermore the straightening process damages the hair, has an unpleasant odour and can cause irritation to the scalp.

An alternative way to straighten the hair is to apply adhesive conditioning materials such as high molecular weight polymers such as silicones (polydialkylsiloxanes) or hydrocarbon oils or waxes to the hair. Although the presence of such materials in compositions may lead to the desired attributes of reduced hair volume, less fluffiness and greater mutual alignment, it also may lead to problems of sensory negatives as it can leave the hair feeling coated, greasy and sticky.

The present invention relates to a hair straightening formulation without the above mentioned negatives.

SUMMARY OF THE INVENTION

In a first aspect, the invention provides an aqueous hair treatment composition comprising:
a) from 0.01% to 10% by weight of the total composition of beeswax; and
b) from 0.01% to 10% by weight of the total composition of a sugar lactone.

The invention also relates to a method of straightening hair by applying to the hair the above described composition.

This invention also relates to the use of the above described composition for straightening hair.

Definitions

By water insoluble it is meant that a material has a solubility in water of 0.1% or less by weight of water at 25° C. By non-volatile it is meant that a material has a vapour pressure of less than 1000 Pa at 25° C.

Viscosities, except where otherwise specified, are dynamic viscosities. These may be measured using a cone and plate rheometer at 25° C. and at a shear rate of 0.01 s$^{-1}$.

Where particles are referred to in the description, the broad definition of particles is meant, indicating that a material is present in a divided form. If the material is a liquid, the particles will be in the form of droplets.

Particle sizes are suitably measured by laser light scattering using an instrument such as a Malvern™ Mastersizer. Particle diameters are expressed as median particle diameters ($D_{50}$).

DETAILED DESCRIPTION OF THE INVENTION

Aqueous Composition

Compositions according to the invention comprise water. Suitably compositions according to the invention comprise 60 or more, preferably 65 or more, more preferably 70 or more percent by weight of water.

Monosaccharide

The composition of the invention comprises a monosaccharide, in particular a sugar lactone, preferably gluconolactone, especially glucono-delta-lactone.

The level of gluconolactone is preferably greater than 0.5 wt % of the total composition, more preferably the level of gluconolactone is from 1 wt % to 8 wt % of the total composition, most preferably from 2 to 6 wt %.

Beeswax

The composition of the present invention comprises beeswax. The wax is available as a commercial by-product of the harvesting and refining of honey. The beeswax is used in the invention preferably in a particulate form as particles with a median ($D_{50}$) diameter of 50 micrometers or less, preferably 20 micrometers or less, more preferably 10 micrometers or less and even more preferably 1 micrometer or less.

The beeswax is suitably present from 0.2% to 4% by weight of the composition, preferably from 0.4% to 3%, more preferably from 0.6% to 2%. The beeswax may be pre-formed into an emulsion or dispersion before addition to the rest of the composition.

A preferred process for incorporating the beeswax into the composition comprises the steps of (i) heating the composition without beeswax to a temperature of 65° C. or higher, preferably 75° C. or higher, (ii) melting the beeswax, (iii) combining the beeswax and the rest of the composition while stirring and (iv) cooling the composition to room temperature, typically 25° C.

Surprisingly, the beeswax is self-emulsifying without the need for vigorous agitation if such a process is followed.

An alternative process for incorporating beeswax into the composition involves the following steps:
i) Preparing an aqueous solution or dispersion of emulsifier at a temperature of 65° C. or more, preferably 70° C. or more, more preferably 80° C. or more.
ii) Preparing molten beeswax at a temperature of 65° C. or more, preferably 70° C. or more, more preferably 80° C. or more.
iii) Mixing and homogenising the liquids of steps (i) and (ii).
iv) Cooling the resulting dispersion to room temperature while stirring gently.

The emulsifier may be any suitable surfactant, but is preferably a blend of cationic surfactant and fatty alcohol, present such that the weight ratio of emulsifier to beeswax is from 1:100 to 1:10, preferably 1:50 to 1:20. A preferred emulsifier system is cetyl trimethylammonium chloride with cetearyl alcohol at a weight ratio of from 1:5 to 5:1.

Silicone Polymer

If present, the silicone polymer in compositions of the invention preferably has a viscosity at 25° C. measured at a shear rate of 0.01 s$^{-1}$ of 600 Pa·s, preferably greater than 1000, more preferably greater than 10 000, even more preferably greater than 100 000 Pa·s.

The silicone polymer may be based upon any suitable polydialkyl or polydiaryl siloxane, but is preferable based upon polydimethylsiloxane. The silicone polymer is preferably water-insoluble and non-volatile.

Suitably, the silicone polymer is present in compositions of the invention as discrete particles with a median diameter ($D_{50}$) of 50 micrometers or less, preferably 20 micrometers or less, more preferably 10 micrometers or less and even more preferably 1 micrometer or less.

In an alternative embodiment of the invention, the silicone polymer may be in the form of a microemulsion, with a particle median diameter of less than 0.15 micrometers.

Preferably the silicone polymer is used as a pre-formed emulsion which can be added to the rest of the composition. This avoids the need for high-shear mixing of the composition to form suitably-sized particles of the silicone polymer in the composition.

It is highly preferred if the silicone polymer is a copolymer of divinyldimethicone and dimethicone having the structure:

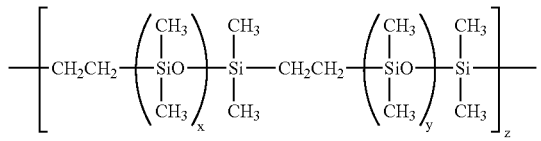

where x, y and z are all integers greater than 1. It is particularly preferred if the copolymer has a viscosity greater than 100 000 Pa·s at a shear rate of 0.01 sec-1). A suitable commercial material supplied as an aqueous emulsion is Dow Corning HMW 2220.

The silicone polymer is suitably present as from 0.1% to 4% by weight of the composition, preferably from 0.3% to 3%, more preferably from 0.5% to 2%.

Aqueous Hair Conditioning Compositions

Suitable compositions for the application of the invention include mousses, lotions and creams. A particularly preferred composition is a cleansing shampoo or shower gel.

Shampoos and Shower Gels

In one particular aspect, compositions according to the invention are cleansing shampoos or shower gels which further comprise one or more cleansing surfactants which are cosmetically acceptable and suitable for topical application to the hair.

Cleansing Surfactant

Suitable cleansing surfactants, which may be used singularly or in combination, are selected from anionic, nonionic, amphoteric and zwitterionic surfactants, and mixtures thereof. Mixtures of anionic and amphoteric surfactants are preferred.

Anionic Cleansing Surfactant

Shampoo compositions according to the invention will typically comprise one or more anionic cleansing surfactants which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic cleansing surfactants for use in shampoo compositions of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, sodium lauryl ether sulphate(n)Eo, (where n ranges from 1 to 3), ammonium lauryl sulphate and ammonium lauryl ether sulphate(n)EO, (where n ranges from 1 to 3).

Mixtures of any of the foregoing anionic cleansing surfactants may also be suitable.

The total amount of anionic cleansing surfactant in shampoo compositions of the invention is generally from 0.5 to 45, preferably from 1.5 to 35, more preferably from 5 to 20 percent by weight of the composition.

Co-surfactant

The composition can include co-surfactants, to help impart aesthetic, physical or cleansing properties to the composition.

A preferred example is an amphoteric or zwitterionic surfactant, which can be included in an amount ranging from 0 to about 8, preferably from 1 to 4 percent by weight.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

Another preferred example is a nonionic surfactant, which can be included in an amount ranging from 0 to 8, preferably from 2 to 5 percent by weight of the composition.

For example, representative nonionic surfactants that can be included in shampoo compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

RO-(G)n wherein R is a branched or straight chain alkyl group which may be saturated or unsaturated and G is a saccharide group. R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in compositions of the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N-(3-methoxypropyl) glucamide.

The composition according to the invention can also optionally include one or more cationic co-surfactants included in an amount from 0.01 to 10, more preferably from 0.05 to 5, most preferably from 0.05 to 2 percent by weight of the composition.

The total amount of cleansing surfactant (including any co-surfactant, and/or any emulsifier) in compositions of the invention is generally from 1 to 25, preferably from 2 to 20, more preferably from 5 to 17 percent by weight of the composition.

A preferred blend of cleansing surfactants is a combination of ammonium lauryl ether sulphate, ammonium lauryl sulphate, PEG 5 cocamide and cocamide MEA (CTFA designations).

Cationic Deposition Polymers

A cationic polymer is a preferred ingredient in shampoo compositions of the invention, for enhancing conditioning performance of the shampoo, if the median particle size of the beeswax or of the silicone polymer is 10 micrometers or less.

The cationic polymer may be a homopolymer or be formed from two or more types of monomers. The molecular weight of the polymer will generally be between 5 000 and 10 000 000 Dalton, typically at least 10 000 and preferably from 100 000 to 2 000 000. The polymers will have cationic nitrogen containing groups such as quaternary ammonium or protonated amino groups, or a mixture thereof.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic conditioning polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have $C_1$-$C_7$ alkyl groups, more preferably $C_{1-3}$ alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic conditioning polymers can comprise mixtures of monomer units derived from amine- and/or quaternary ammonium-substituted monomer and/or compatible spacer monomers.

Suitable cationic conditioning polymers include, for example:

copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);

copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);

cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo- and copolymers of unsaturated carboxylic acids having from 3 to 5 carbon atoms, (as described in U.S. Pat. No. 4,009,256);

cationic polyacrylamides (as described in WO95/22311).

Other cationic conditioning polymers that can be used include cationic polysaccharide polymers, such as cationic cellulose derivatives, cationic starch derivatives, and cationic guar gum derivatives. Suitably, such cationic polysaccharide polymers have a charge density from 0.1 to 4 meq/g.

Cationic polysaccharide polymers suitable for use in compositions of the invention include those of the formula:

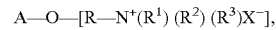

$$A\text{—}O\text{—}[R\text{—}N^+(R^1)(R^2)(R^3)X^-],$$

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (commercially available from Rhone-Poulenc in their JAGUAR trademark series).

Examples are JAGUAR $C_{13}S$, which has a low degree of substitution of the cationic groups and high viscosity. JAGUAR $C_{15}$, having a moderate degree of substitution and a low viscosity, JAGUAR $C_{17}$ (high degree of substitution, high viscosity), JAGUAR $C_{16}$, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic conditioning polymer is selected from cationic cellulose and cationic guar derivatives. Particularly preferred cationic polymers are JAGUAR C13S, JAGUAR $C_{15}$, JAGUAR $C_{17}$ and JAGUAR $C_{16}$ and JAGUAR $C_{16}2$.

The cationic conditioning polymer will generally be present in compositions of the invention at levels of from 0.01 to 5, preferably from 0.02 to 1, more preferably from 0.04 to 0.5 percent by weight of the composition.

Suspending Agents

Optionally, the compositions according to the invention may further comprise from 0.1 to 10 percent by weight, preferably from 0.6% to 6%, of a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol (trade mark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

However, if the median diameter of the particles of the beeswax and of the silicone polymer is less than 10 micrometers, it is preferred if the composition is free of suspending agent, by which is meant that compositions of the invention comprise less than 0.01% by weight of suspending agent. This is because suspending agents may deposit onto the hair, leading to a coated feel for some users.

Other Ingredients

Compositions according to the invention may additionally contain other ingredients suitable for use in hair cleansing and conditioning compositions. Other hydrophobic, water-insoluble conditioning oils may be included in addition to those of the invention.

The compositions of the present invention may also contain adjuvants suitable for hair care. Generally such ingredients are included individually at a level of up to 2 percent by weight of the total composition.

Among suitable hair care adjuvants, are natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts. A particularly preferred combination of natural hair root nutrients for inclusion in compositions of the invention is isoleucine and glucose. A particularly preferred amino acid nutrient is arginine. Another suitable adjuvant is glycolic acid.

Mode of Use

The compositions of the invention are primarily intended for topical application to the hair and/or scalp of a human subject in rinse-off or leave-on compositions. The compositions are used to provide straightening, reduced volume and/or fluffiness of hairstyle after the hair is dried. In order to achieve the benefits it is not necessary to dry the hair using a heated air hair-drying apparatus, and it is preferred if the hair is allowed to dry naturally after towelling and brushing.

EXAMPLES

TABLE 1

Weight % in table 1 refers to the actual active chemical in the composition, and not the dilute raw material.

| | | | weight % | |
|---|---|---|---|---|
| Chemical name | Trade Name | Supplier | A | 1 |
| Sodium laureth (2 EO) sulphate | Empicol ESB70 | Albright & Wilson | 14 | 14 |
| Coco amidopropyl betaine | Tegobetaine CK | Goldschmidt | 2 | 2 |
| Guar Hydroxypropyl Trimonium Chloride | Jaguar C13S | Rhone Poulenc | 0.2 | 0.2 |
| Divinyldimethicone/ dimethicone copolymer[1] | HMW2220 | Dow Corning | 2.0 | 2.0 |
| Beeswax | | Koster Keunen | — | 1.5 |
| Gluconolactone | | Aldrich | — | 4.0 |
| Ethylene Glycol Distearate | PK3000AM | COGNIS | 1 | 1 |
| Formaldehyde | Formalin | Mallinkropt | 0.1 | 0.1 |
| Water | — | — | To 100 | To 100 |

[1]Silicone polymer added as 60% by weight active emulsion

Laser Volume Analysis—

2 g of 25 cm long Asian hair switches were degreased using diethyl ether and rinsed in water. Using 5 switches per treatment, 0.2 ml of each of the shampoo compositions (either A, B or 1) was spread along the length of the switch and agitated for 30 seconds, followed by a rinse for 30 seconds. The washing process was repeated again using 0.2 ml of shampoo placed along the length of the switch and agitated for 30 seconds, followed by a rinse in water for 1 minute. The switches were combed through whilst suspended vertically from a clamp stand, then rinsed with a spray of water from a water bottle. The switches were then allowed to dry naturally overnight.

After drying, each switch was suspended vertically from a clamp stand and a 2 mW, 632.8 nanometer wavelength Helium-Neon laser shone perpendicular to the untouched switch, 5 cm from the bottom of the switch, and the illuminated image recorded onto an optical disc using a 35 mm camera.

Image analysis was carried out on the resulting image to estimate the spread of each hair switch 5 cm from the bottom of each switch (expressed as mean radial distribution in mm). The smaller the value for the spread, the lower the apparent volume of the switch and the greater the straightness of the fibres.

The mean results obtained for the radial distribution were:

| Example 1 | 13.2 |
|---|---|
| Example A | 16 |

Hence the product according to the invention is shown to give straighter hair with improved manageability.

The invention claimed is:

1. A method of straightening hair by applying to the hair an aqueous hair treatment composition comprising:
   a) from 0.01% to 4% 0.4% to 3% by weight of the total composition of beeswax;
   b) from 0.01% to 10% 2% to 6% by weight of the total composition of gluconolactone;
   c) from 5% to 20% by weight of the total composition sodium lauryl ether sulphate (EO)n, where n is 1 to 3;
   d) 1.0% to 4% by weight coocoamidopropylbetaine;
   e) 0.04% to 0.5% by weight guar hydroxypropyltrimonium chloride;
   f) 0.6% to 6% by weight ethylene glycol distearate; and
   g) 0.3% to 3% by weight silicone polymer.

2. A method according to claim 1 wherein the beeswax and the silicone polymer are present in an aqueous hair treatment composition in the form of particles with a median diameter ($D_{50}$) of 50 micrometers or less.

3. A method according to claim 1 wherein said aqueous hair treatment composition is a rinse-off composition.

* * * * *